United States Patent [19]

Russo

[11] Patent Number: 5,083,561
[45] Date of Patent: Jan. 28, 1992

[54] TRACHEAL SUCTION CATHETER

[76] Inventor: Ronald D. Russo, 8 Candleberry Rd., Barrington, R.I. 02806

[21] Appl. No.: 538,250

[22] Filed: Jun. 14, 1990

[51] Int. Cl.$^5$ .............................................. A61M 16/00
[52] U.S. Cl. ........................... 128/207.16; 128/207.14; 128/912; 604/119
[58] Field of Search ...................... 128/202.16, 207.14, 128/912, 207.15, 207.16; 604/119; 606/151, 157, 158; 251/10

[56] References Cited

U.S. PATENT DOCUMENTS

| | | | |
|---|---|---|---|
| 455,392 | 7/1891 | Ellis | 251/10 |
| 2,930,570 | 3/1960 | Leed | 251/10 |
| 3,902,800 | 9/1975 | Dryden | 126/207.14 |
| 3,912,795 | 10/1975 | Jackson | 128/207.14 |
| 3,991,762 | 11/1976 | Radford | 604/119 |
| 4,351,328 | 9/1982 | Bodai | 128/912 |
| 4,453,295 | 6/1984 | Laszczower | 606/157 |
| 4,488,548 | 12/1984 | Agdanowski | 128/207.15 |
| 4,588,160 | 5/1986 | Flynn et al. | 606/157 |
| 4,638,539 | 1/1987 | Palmer | 128/207.16 |
| 4,850,350 | 7/1989 | Jackson | 128/207.16 |
| 4,852,563 | 8/1989 | Gross | 128/912 |
| 4,919,127 | 4/1990 | Pell | 128/912 |
| 4,953,847 | 9/1990 | Poole, Jr. | 128/207.14 |
| 4,967,743 | 11/1990 | Lambert | 128/207.16 |

Primary Examiner—Paul J. Hirsch
Attorney, Agent, or Firm—Robert J. Doherty

[57] ABSTRACT

A suction device for removing material from the trachea of a patient during ventilation comprising, a catheter having an internal lumen and opposed front and rear ends with the front end including a suction opening, front and rear couplings supporting the catheter and a protective sleeve normally enclosing the catheter and in turn connected to the front and rear couplings, the catheter is fixedly connected at its rear end to the rear coupling, the front coupling includes an internal seal for slidable receipt of the outer surface of the catheter. Thus, the catheter front end may be inserted into and withdrawn from the trachea of said patient. The rear coupling includes an irrigation port in turn communicating with the catheter lumen whereby lavage fluid may be injected into the port so as to wash the lumen and to directly irrigate the patient's trachea through said suction opening.

9 Claims, 3 Drawing Sheets

TRACHEAL SUCTION CATHETER

BACKGROUND OF THE INVENTION

The use of a suction catheter to remove accumulated mucous from a patients airway is widely used and known. Sterile handling of the catheter and connection to the ventilating machine have also been proposed and discovered. Dryden, in U.S. Pat. No. 3,902,500, first disclosed a catheter with a sleeve and a device which first addressed the sterile technique and ventilator problems.

One of the main problems with Dryden was the fact that when it was connected to the ventilating machine that oxygen being delivered to the patient would inflate the protective sleeve and oxygen was lost through the open valve.

To solve these problems, Radford, U.S. Pat. No. 3,991,762, proposed a frontal seal which prevented the sleeve or envelope from inflating and a rear valve mechanism which prevented oxygen from escaping into the atmosphere.

Most recently, Palmer, U.S. Pat. No. 4,696,296, disclosed an Aspirating/Ventilating Apparatus and Method with a protective catheter sleeve, a frontal catheter seal, an irrigation port located frontally and a rather complex normally closed proximal valve mechanism.

The prior art is discussed in considerable detail in all these patents.

To my knowledge, the device of Palmer is the only one which is commercially available although it is very expensive (approximately $12.00 each) versus a regular suction catheter without the Palmer features of around $0.50 each.

In spite of the expense of Palmer many hospitals have begun using the Palmer device since its catheter sleeve offers contamination protection to the user and the device once attached to the ventilator can be reused to suction the patient.

Protection to the healthcare worker from coming in contact with body secretions is very important because of possible Hipatitus or HIV infection from contact with body fluids.

The device of Palmer does offer that protection to the user and has proven successful in spite of the expense to the healthcare system.

BRIEF SUMMARY AND OBJECTS OF THE INVENTION

With the foregoing in mind, the present invention offers all the advantages of the prior art with additional features and at lower hospital cost.

The present invention among other things, is unitized to prevent separation and the danger of aspiration of loose components, is less expensive, more comfortable for the patient, provides more effective and rapid suction, less clogging of the device, and more thorough flushing of the inside of the catheter to prevent the growth of potentially harmful organisms.

Accordingly, it is a primary object to provide a device which is safer, more convenient to use, less expensive, and yet provides protection to the user from body fluid contact.

An objective of the invention is to provide a ventilator adapter which will swivel in response to the user for greater patient comfort.

Another objective is to provide a completely unitized assembly to eliminate any separation of any component.

Another objective is to provide a much less expensive and more effective normally closed suction control device.

A further objective to the suction control device is to be external to the fluid flow path to prevent internal blockages and clogging.

Another object is to provide a catheter flushing element which directly accesses the inside of the catheter to thoroughly flush the catheter to prevent blockage and eliminate organism contamination from residual mucous.

Another important objective is to provide a completely closed suction catheter system which prevents user contact with body fluids.

Another objective is to provide a device which is positioned comfortably on the patient when not in use.

DETAILED DESCRIPTION OF THE ILLUSTRATED EMBODIMENT

Figure 1:
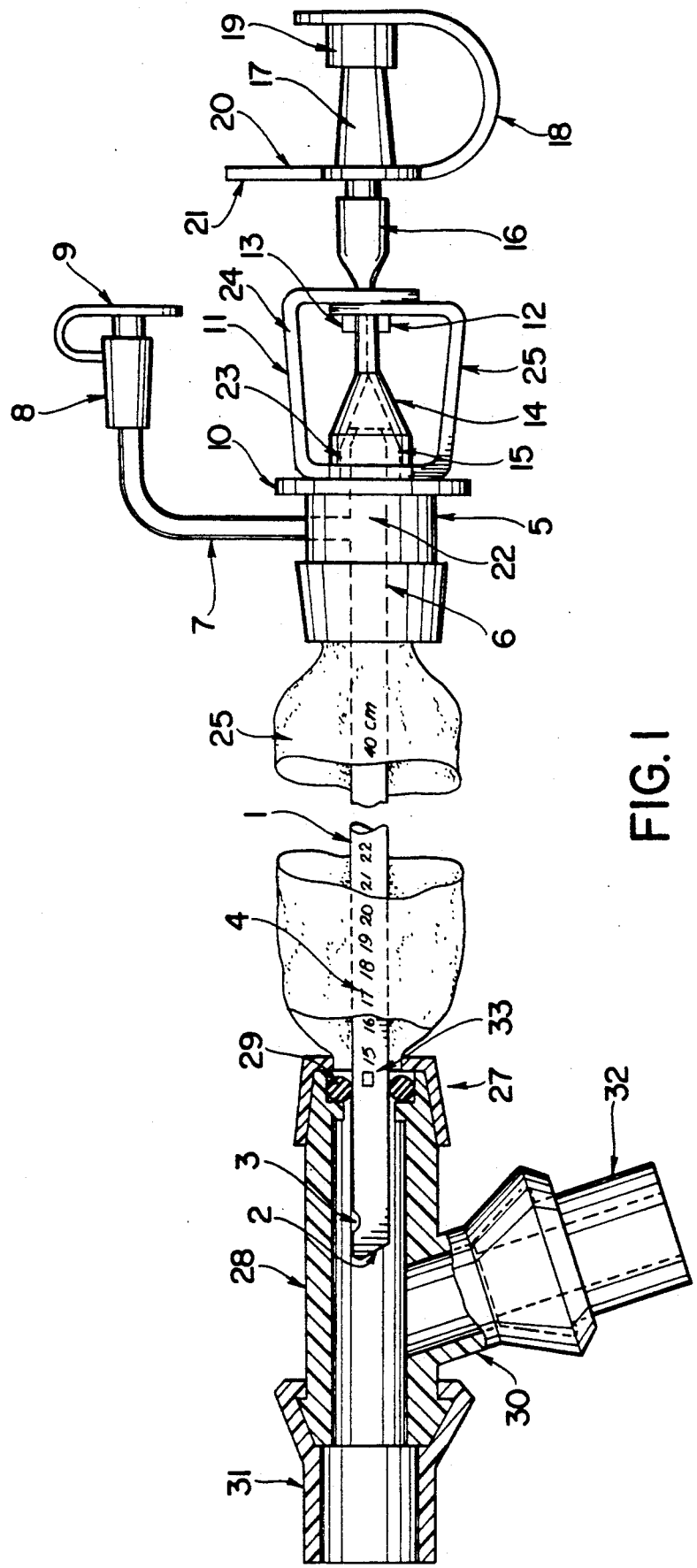

FIG. 1 is a side view of the catheter assembly.

Figure 2:
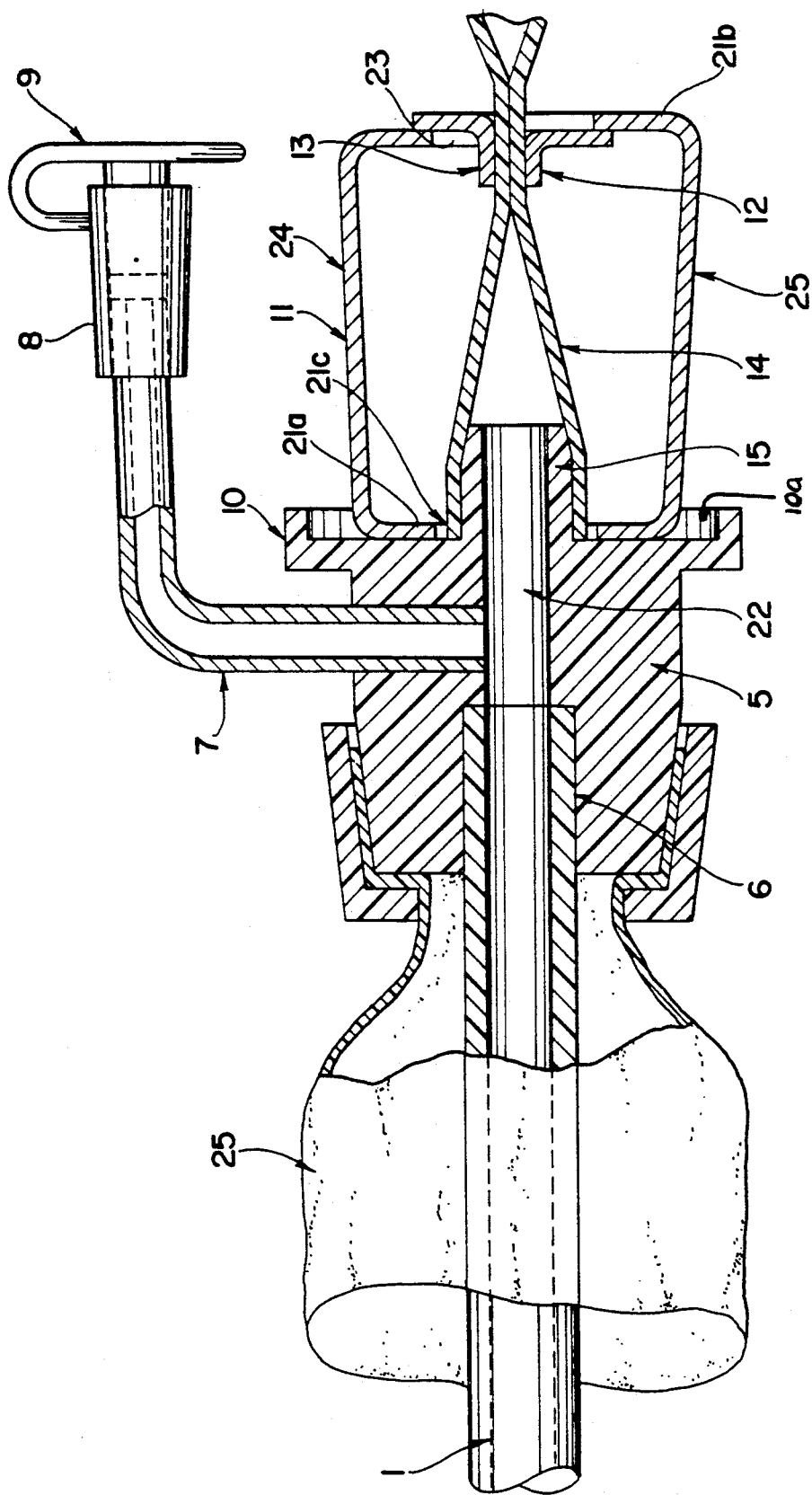

FIG. 2 in an enlarged sectional view of the lavage port.

Figure 3:
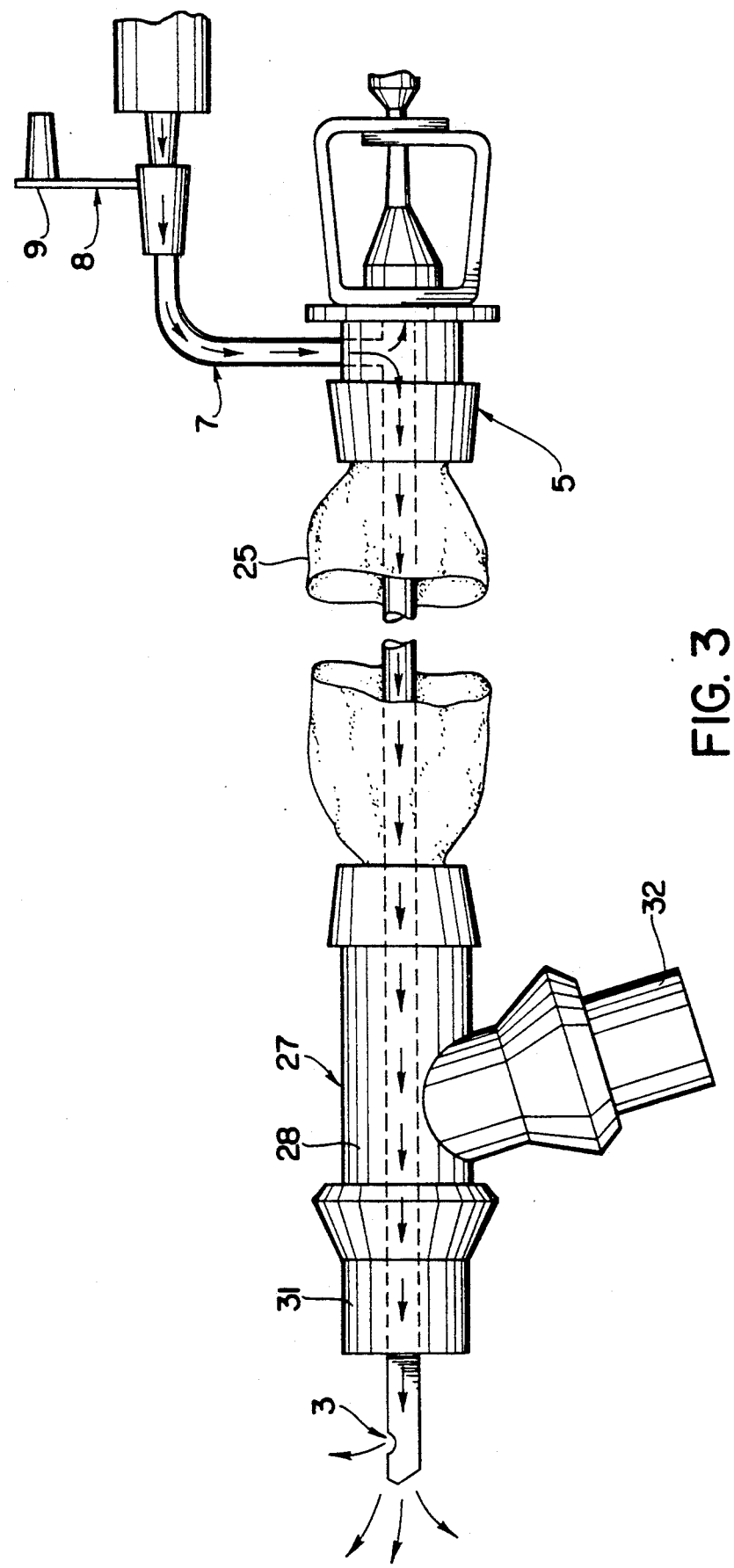

FIG. 3 is a side view showing the catheter advanced and lavage at catheter tip.

FIG. 1 is a side view showing flexible catheter 1 typically extruded from PVC plastic. The or front end distal tip of the catheter 2 is rounded smooth with a side vent hole 3.

The catheter is graduated 4 with centimeter markings to show the depth of insertion into the trachea. Injection molded coupling 5 is made from rigid PVC. The prodimal or rear end of catheter 1 is solvent bonded into coupling rear 5 at joint 6. A side port 7 accesses internal lumen 22 on the coupling. Port seven is extruded form flexible PVC. Solvent bonded onto 7 is an injection molded PVC connector 8 which will accept any luer tip syringe. Closer cap 9 is normally closed on connecter 8.

A collar or flange 10 having a recess 10a is provided on coupling 5 to prevent inadvertent activation of a spring steel external clamp 11 having clamp leafs 24 and 25. The clamp 11 includes a base 21a in turn having an opening 21c through which rubber or silicone tubing 14 passes. Tubing 14 is press fit onto coupling over stem 15. Thus, the stem 15 and the tubing 14 thereover frictionally position the clamp 11 as shown. The leafs in turn have inwardly extending fingers 21b in turn each provided with an opening 23. The fingers 21b in turn include a forwardly extending integral tab at the inner periphery of the openings 23. These tabs 12 and 13 are normally closed, that is, biased to contact each other so when the tubing 14 is inserted through openings 23, the tabs 12 and 13 press down on the tubing to completely close off the fluid path.

Note clamp 11 acts externally on tubing 14 such that when clamp leafs 24 and 25 are pressed down by the user that resilient tubing 14 opens up to permit fluid flow through the tubing. The clamp can be made in one piece of spring steel.

The rear of tubing 14 is press fit onto suction connector 17 at joint 16. The connector is injection molded of rigid polypropylene. An integral strap 18 attaches to closer cap 19 to close off connector 17.

Strap extension 20 has a molded in hole 21 through which a simple safety pin can pass through. The safety pin can attach to the patients gown to hold the device in place when not in use.

FIG. 1 depicts a complete closed tracheal suction system. An extruded polyethlene envelope 25 is attached to coupling 5 using ultrasonic welding.

Envelope 25 is attached at its distal portion to swivel adapter 30 at a front coupling or joint 27 which also ultrasonically welds the envelope to the swivel adapter.

The adapter is molded from clear rigid PVC with front swivel 31 which directly attaches to the tracheal tube.

Side swivel 32 attaches to the ventilator tubing. Press fit into the adapter is neoprene "O" ring 29 through which the front portion of the catheter 1 is inserted.

The O ring forms a seal around the catheter to prevent oxygen from the ventilator inflating envelope 25.

Further since rear clamp 11 is normally closed no oxygen can escape to atmosphere, e.g. via opening 3.

During use the device of FIG. 1. is attached to the patient at front swivel 31.

The catheter can be advanced into the front swivel down into the patients trachea and the patient suctioned as often as desired without disconnecting the ventilator from side swivel 32.

Black line 33 is an indicator line which indicates to the user that the catheter is fully retracted and not inside the patient.

When suction connector 17 is connected to a source of suction no suction is applied to the catheter tip until clamp 11 if fully depressed open.

The passageway of silicone tubing 14 and connector 17 is larger than the catheter internal diameter such that any thick mucous plugs which pass through the catheter will easily flow through the passageway of the tubing and connector and will not clog the device.

Most importantly the silicone tubing 14 has a smooth uninterrupted passageway wherein suctioned mucous will not become clogged.

The prior art of Palmer has a very complex internal mechanism which readily becomes clogged with thick secretions making the entire system non-functional.

Further, all the prior art of enveloped catheters have an irrigation port located in a front coupling which accesses only the outside of the catheter.

Mucous plugs can become lodged in the inside of the catheter or in the valve mechanism of the prior art with no means of internal flushing of the catheter and the inside of the valve.

The present invention shows flushing port 7 located in the rear coupling 5 to effectively flush both the inside of the catheter and the entire internal passageways of the device.

Cap 9 is readily opened and 5 to 8 cc's of water or saline will effectively flush the device.

Encrusted and lodged mucous in the prior art catheters and valve mechanism can breed viruses and bacteria which can be reintroduced at the next suctioning procedure.

With the present invention instantaneous flushing of the entire passageway takes place during flushing to prevent organism build-up.

All the normally closed valves of the prior art closed systems are internal valve devices which are difficult to manufacture, expensive and block the fluid flow of thick secretions often becoming clogged. This is why the Palmer device must be disassembled wherein the present invention is unitized.

As can be seen the device is simpler, easier to use, and provides for more effective suctioning and flushing of the device at less expense to the institution.

Appropriate instructions for the use of the present closed track suction system are as follows:

SET UP

1. Attach suction connection to wall suction.
2. Turn on wall suction before attaching the system to the patient, depress suction control clamp while setting suction to desired level.
3. Attach ventilation circuit to side swivel opening.
4. Connect front 15 mm I.D. end to patient trach tube.
5. Insure irrigation port is closed.
6. Attach a safety pin to cap hole, if desired.

TO SUCTION PATIENT

1. Hold onto swivel adapter with one hand and advance catheter with opposite hand through the sleeve.
2. Apply intermittent suction by depressing suction control clamp.
3. Upon completion, fully retract the catheter until black line on catheter is visible.
4. Flush catheter by introducing solution into the irrigation port (5 to 8 MLs)
5. Depress suction control clamp after instilling solution.
6. Turn off wall suction, cap, and pin to patient gown.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims. For instance as a specific example, the terms "front coupling" and "rear coupling" as used herein refer to the means respectively needed for operational connection to the endotracheal tube in the front and to the suction control valve in the rear. Thus, front and rear coupling are broad terms.

I claim:

1. A suction device for removing material from the trachea of a patient during ventilation comprising, a catheter having an internal lumen and opposed front and rear ends with the front end including a suction opening, front and rear couplings supporting said catheter and a protective sleeve normally enclosing said catheter and in turn connected to said front and rear couplings, said catheter fixedly connected at its rear end to said rear coupling, said front coupling including an internal seal for slidable receipt of the outer surface of said catheter whereby said catheter front end may be inserted into and withdrawn from the trachea of said patient, and said rear coupling including an irrigation port in turn communicating with said catheter lumen whereby lavage fluid may be injected into said port so as to wash said lumen and to directly irrigate the patient's trachea through said suction opening.

2. The device of claim 1, said sleeve is in the form of an expandible, collapsible plastic sheath normally enclosing said catheter and having opposed front and rear ends respectively sealingly attached to said front and rear couplings, said rear coupling movable towards said front coupling when said catheter is forwardly advanced with accompanying collapse of said sleeve as when the catheter front end is inserted into the patient's trachea.

3. The device of claim 1, said irrigation port having closure means.

4. The device of claim 1, including means connected to said rear coupling for applying suction to said catheter.

5. The device of claim 4, said suction applying means including a tubular member connectable at one end to a suction source and connected to said rear coupling at the other end thereof and a valve member for effectively biasing said tubular member in a normally closed position.

6. The device of claim 5, said rear coupling including a passageway operationally connecting said catheter lumen with said tubular member and to said suction source when said valve member is opened.

7. The device of claim 1, said irrigation port is connected to said rear coupling passageway.

8. The device of claim 6, said rear coupling including a front portion attached to said sleeve and a rearwardly disposed flange in turn supporting the base of a leaf clamp comprising said valve member, said rear coupling further including a stem rearwardly extending from said flange for receipt of said tubular member.

9. The device of claim 1, said device further including an adapter capable of attachment to a tracheal tube connected to said front coupling, said adapter having a ventilator side port adapted for connection to a ventilator and wherein said internal seal through which said catheter tube is slidably received prevents inflation of said sleeve during operation of the ventilator when the adapter is connected to the patient.

* * * * *

REEXAMINATION CERTIFICATE (2015th)
United States Patent [19]
Russo

[11] B1 5,083,561
[45] Certificate Issued    May 18, 1993

[54] TRACHEAL SUCTION CATHETER

[76] Inventor: Ronald D. Russo, 8 Candleberry Rd., Barrington, R.I. 02806

Reexamination Request:
No. 90/002,645, Feb. 14, 1992

Reexamination Certificate for:
Patent No.: 5,083,561
Issued: Jan. 28, 1992
Appl. No.: 538,250
Filed: Jun. 14, 1990

[51] Int. Cl.⁵ .................................... A61M 16/00
[52] U.S. Cl. ........................... 128/207.16; 128/207.14; 128/912; 604/119
[58] Field of Search ............... 604/167, 171, 119; 128/202.16, 207.14, 207.15, 207.16, 912; 606/157; 251/10

[56]         References Cited
U.S. PATENT DOCUMENTS

| | | | |
|---|---|---|---|
| 455,392 | 7/1891 | Ellis | 251/10 |
| 3,991,762 | 11/1976 | Radford | 604/119 |
| 4,850,350 | 7/1989 | Jackson | 128/207.16 |
| 4,953,547 | 9/1990 | Poole, Jr. | 128/207.14 |
| 5,073,164 | 12/1991 | Hollister et al. | 604/43 |

*Primary Examiner*—Paul J. Hirsch

[57]    ABSTRACT

A suction device for removing material from the trachea of a patient during ventilation comprising, a catheter having an internal lumen and opposed front and rear ends with the front end including a suction opening, front and rear couplings supporting the catheter and a protective sleeve normally enclosing the catheter and in turn connected to the front and rear couplings, the catheter is fixedly connected at its rear end to the rear coupling, the front coupling includes an internal seal for slidable receipt of the outer surface of the catheter. Thus, the catheter front end may be inserted into and withdrawn from the trachea of said patient. The rear coupling includes an irrigation port in turn communicating with the catheter lumen whereby lavage fluid may be injected into the port so as to wash the lumen and to directly irrigate the patient's trachea through said suction opening.

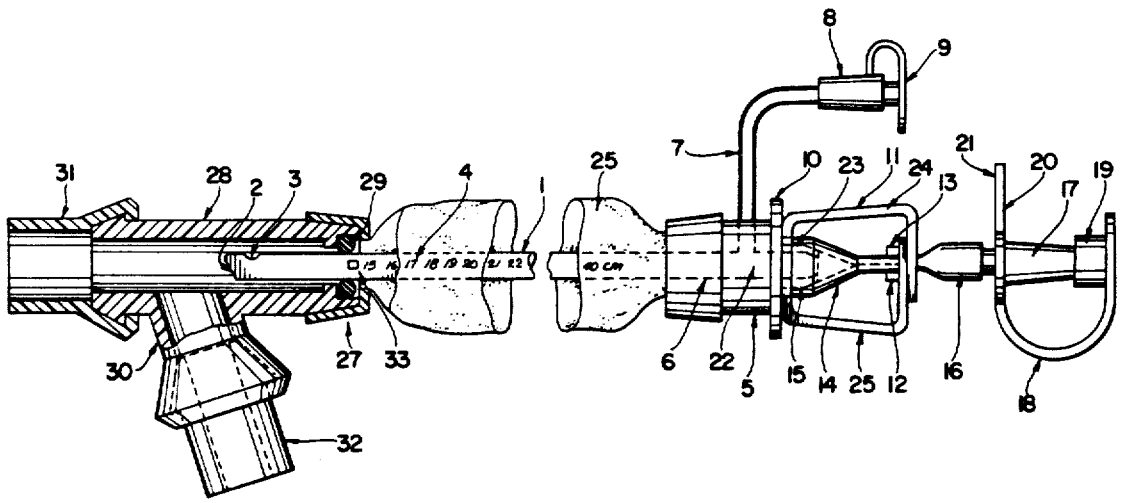

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-9 are confirmed.

New claims 10-30 are added and determined to be patentable.

10. The device of claim 4, said means for applying suction to said catheter and said irrigation port being separate and independent of each other such that the patient may be simultaneously suctioned and lavaged.

11. A suction device for removing material from the trachea of a patient during ventilation comprising a catheter having an internal lumen and opposed front and rear ends with the front end including a suction opening, front and rear couplings supporting said catheter and a protective sleeve normally enclosing said catheter and in turn connected with said front and rear couplings, said catheter fixedly connected at its rear end to said rear coupling, said front coupling including an internal seal for slidable receipt of the outer surface of said catheter whereby said catheter front end may be inserted into and withdrawn from the trachea of said patient, and said rear coupling including an irrigation port in turn communicating with said catheter lumen at said rear coupling whereby lavage fluid may be injected into said port so as to directly wash said lumen in a rear to front catheter flow direction and to directly irrigate the patient's trachea by passing out of the catheter through said suction opening.

12. The device of claim 11, said sleeve is in the form of an expandable, collapsible plastic sheath normally enclosing said catheter and having opposed front and rear ends respectively sealingly attached to said front and rear couplings, said rear coupling movable towards said front coupling when said catheter is forwardly advanced with accompanying collapse of said sleeve as when the catheter front end is inserted into the patient's trachea.

13. The device of claim 11, said irrigation port having closure means.

14. The device of claim 11 including means connected to said rear coupling for applying suction to said catheter.

15. The device of claim 14, said suction applying means including a tubular member connectable at one end to a suction source and connected to said rear coupling at the other end thereof and a valve member for effectively biasing said tubular member in a normally closed position.

16. The device of claim 15, said rear coupling including a passageway operationally connecting said catheter lumen with said tubular member and to said suction source when said valve member is opened.

17. The device of claim 11, said irrigation port is connected to said rear coupling passageway.

18. The device of claim 16, said rear coupling including a front portion attached to said sleeve and a rearwardly disposed flange in turn supporting the base of a leaf clamp comprising said valve member, said rear coupling further including a stem rearwardly extending from said flange for receipt of said tubular member.

19. The device of claim 11, said device further including an adapter capable of attachment to a tracheal tube connected to said front coupling, said adapter having a ventilator side port adapted for connection to a ventilator and wherein said internal seal through which said catheter tube is slidably received prevents inflation of said sleeve during operation of the ventilator when the adapter is connected to the patient.

20. The device of claim 14, said means for applying suction to said catheter and said irrigation port being separate and independent of each other such that the patient may be simultaneously suctioned and lavaged.

21. A suction device for removing material from the trachea of a patient during ventilation comprising a catheter having a single internal lumen and opposed front and rear ends with the front end including a suction opening, front and rear couplings supporting said catheter and a protective sleeve normally enclosing said catheter and in turn connected to said front and rear couplings, said catheter fixedly connected at its rear end to said rear coupling, said front coupling including an internal seal for slidable receipt of the outer surface of said catheter whereby said catheter front end may be inserted into and withdrawn from the trachea of said patient, and said rear coupling including an irrigation port in turn communicating directly with said catheter lumen at said rear coupling whereby lavage fluid may be injected into said port so as to directly wash said lumen in a rear to front catheter flow direction and to directly irrigate the patient's trachea by passing out of the catheter through said suction opening.

22. The device of claim 21, said sleeve is in the form of an expandable, collapsible plastic sheath normally enclosing said catheter and having opposed front and rear ends respectively sealingly attached to said front and rear couplings, said rear coupling movable towards said front coupling when said catheter is forwardly advanced with accompanying collapse of said sleeve as when the catheter front end is inserted into the patient's trachea.

23. The device of claim 21, said irrigation port having closure means.

24. The device of claim 21 including means connected to said rear coupling for applying suction to said catheter.

25. The device of claim 24 said suction applying means including a tubular member connectable at one end to a suction source and connected to said rear coupling at the other end thereof and a valve member for effectively biasing said tubular member in a normally closed position.

26. The device of claim 25 said rear coupling including a passageway operationally connecting said catheter lumen with said tubular member and to said suction source when said valve member is opened.

27. The device of claim 21, said irrigation port is connected to said rear coupling passageway.

28. The device of claim 25 said rear coupling including a front portion attached to said sleeve and a rearwardly disposed flange in turn supporting the base of a leaf clamp comprising said valve member, said rear coupling further including a stem rearwardly extending from said flange for receipt of said tubular member.

29. The device of claim 21, said device further including an adapter capable of attachment to a tracheal tube connected to said front coupling, said adapter having a ventilator side port adapted for connection to a ventilator and wherein said internal seal through which said catheter tube is slidably received prevents inflation of said sleeve during operation of the ventilator when the adapter is connected to the patient.

30. The device of claim 24, said means for applying suction to said catheter and said irrigation port being separate and independent of each other such that the patient may be simultaneously suctioned and lavaged.

* * * * *